(12) United States Patent
Spotnitz et al.

(10) Patent No.: US 11,052,172 B2
(45) Date of Patent: Jul. 6, 2021

(54) HEMOSTATIC FLOWABLE (71) Applicant: BIOM'UP, Saint-Priest (FR)

(72) Inventors: William Spotnitz, Gainesville, FL (US); Valérie Centis, Lyons (FR); Doris Moura Campos, Bourgoin Jallieu (FR); Alexia De Gasperis, Saint Genis Laval (FR)

(73) Assignee: BIOM'UP FRANCE SAS, Saint-Priest (FR)

(*) Notice: Subject to any disclaimer, the term of this patent is extended or adjusted under 35 U.S.C. 154(b) by 0 days.

(21) Appl. No.: 16/324,637

(22) PCT Filed: Aug. 11, 2017

(86) PCT No.: PCT/EP2017/070428
§ 371 (c)(1),
(2) Date: Feb. 11, 2019

(87) PCT Pub. No.: WO2018/029340
PCT Pub. Date: Feb. 15, 2018

(65) Prior Publication Data
US 2019/0167840 A1    Jun. 6, 2019

(30) Foreign Application Priority Data

Aug. 12, 2016 (EP) .................................. 16184119

(51) Int. Cl.
*A61L 26/00* (2006.01)

(52) U.S. Cl.
CPC ......... *A61L 26/0052* (2013.01); *A61L 26/008* (2013.01); *A61L 26/0066* (2013.01); *A61L 2300/232* (2013.01); *A61L 2300/236* (2013.01); *A61L 2300/252* (2013.01); *A61L 2300/418* (2013.01); *A61L 2400/04* (2013.01); *A61L 2400/06* (2013.01)

(58) Field of Classification Search
CPC .............. A61L 26/0052; A61L 26/008; A61L 26/0066; A61L 26/06; A61L 2300/232; A61L 2300/236; A61L 2300/252; A61L 2300/418
See application file for complete search history.

(56) References Cited

U.S. PATENT DOCUMENTS

| | | | |
|---|---|---|---|
| 4,427,651 A | 1/1984 | Stroetmann | |
| 4,891,359 A | 1/1990 | Saferstein et al. | |
| 4,942,153 A | 7/1990 | Fernandez | |
| 5,413,571 A * | 5/1995 | Katsaros | A61B 17/0057 128/899 |
| 6,280,727 B1 | 8/2001 | Prior et al. | |
| 7,119,062 B1 * | 10/2006 | Alvis | A61K 9/0024 514/17.2 |
| 9,283,187 B2 | 3/2016 | Gagnieu et al. | |
| 9,662,374 B2 | 5/2017 | Gagnieu et al. | |
| 10,046,034 B2 | 8/2018 | Gagnieu et al. | |
| 2005/0147679 A1 | 7/2005 | Petito et al. | |
| 2005/0208114 A1 | 9/2005 | Petito et al. | |
| 2006/0019868 A1 * | 1/2006 | Pendharkar | A61K 31/715 514/200 |
| 2006/0051377 A1 * | 3/2006 | First | A61K 38/4893 424/239.1 |
| 2006/0073207 A1 | 4/2006 | Masters et al. | |
| 2007/0009578 A1 | 1/2007 | Moller et al. | |
| 2007/0140984 A1 | 6/2007 | Kusano et al. | |
| 2008/0021374 A1 | 1/2008 | Kawata | |
| 2009/0062849 A1 | 3/2009 | Dowling et al. | |
| 2009/0192429 A1 | 7/2009 | Daniels et al. | |
| 2012/0040119 A1 | 2/2012 | Gagnieu et al. | |
| 2012/0148633 A1 * | 6/2012 | Sun | A61P 17/10 424/400 |

(Continued)

FOREIGN PATENT DOCUMENTS

| | | |
|---|---|---|
| CA | 2485268 A1 | 11/2003 |
| CN | 1554448 A | 12/2004 |
| CN | 1709507 A | 12/2005 |

(Continued)

OTHER PUBLICATIONS

Avery et al., "The Effects of the Maillard Reaction on the Physical Properties and Cell Interactions of Collagen", Pathologie Biologie, vol. 54, 2006, pp. 387-395, XP024926173.

European Search Report, dated Aug. 5, 2011, for European Application No. 11305492.8.

Written Opinion of the International Searching Authority and International Search Report, dated Jul. 17, 2012, for International Application No. PCT/EP2012/057647.

Buehler, "Nature Designs Tough Collagen: Explaining the Nanostructure of Collagen Fibrils," PNAS, vol. 103, No. 33, Aug. 15, 2006, pp. 12285-12290.

(Continued)

*Primary Examiner* — Ali Soroush (74) *Attorney, Agent, or Firm* — Birch, Stewart, Kolasch & Birch, LLP (57) ABSTRACT

The invention relates to a kit to prepare an hemostatic flowable comprising: —A hemostatic powder having a composition comprising: ○non-cross-linked collagen of the fibrillar type comprising a content of fibrous collagen and/or fibrillar collagen of at least 70% by weight relative to the total weight of the collagen; ○at least one monosaccharide; and ○at least one glycosaminoglycan; —A saline solution to be mixed with the hemostatic powder in order to form the hemostatic flowable. The invention also relates to a method for preparing an hemostatic flowable with such a kit, comprising the steps of: a. Providing the hemostatic powder in a container; b. Adding a quantity of the saline solution in the container enclosing the hemostatic powder, closing and shaking said container in order to promote hydration of the hemostatic powder to form the hemostatic flowable.

30 Claims, 3 Drawing Sheets

(56) References Cited

U.S. PATENT DOCUMENTS

2014/0018729 A1\* 1/2014 Foster .................. A61M 5/00
604/58

FOREIGN PATENT DOCUMENTS

| | | |
|---|---|---|
| CN | 1921896 A | 2/2007 |
| CN | 101001649 A | 7/2007 |
| CN | 101272790 A | 9/2008 |
| CN | 101757614 A | 6/2010 |
| CN | 101837143 A | 9/2010 |
| CN | 101883545 A | 11/2010 |
| DE | 19520575 A1 | 12/1996 |
| EP | 0145970 A2 | 6/1985 |
| EP | 1580229 A1 | 9/2005 |
| EP | 1905443 A1 | 4/2008 |
| FR | 2944706 A1 | 10/2010 |
| JP | 2003-62057 A | 3/2003 |
| WO | WO 93/21857 A1 | 11/1993 |
| WO | WO 95/03786 A2 | 2/1995 |
| WO | WO 98/57678 A2 | 12/1998 |
| WO | WO 00/10540 A1 | 3/2000 |
| WO | WO 01/97871 A2 | 12/2001 |
| WO | WO 01/97873 A2 | 12/2001 |
| WO | WO 02/098223 A1 | 12/2002 |
| WO | WO 03/026709 A1 | 4/2003 |
| WO | WO 03/094983 A1 | 11/2003 |
| WO | WO 2005/016257 A2 | 2/2005 |
| WO | WO 2005/072700 A2 | 8/2005 |
| WO | WO 2005/092968 A1 | 10/2005 |
| WO | WO 2005/115252 A1 | 12/2005 |
| WO | WO 2009/109963 A1 | 9/2009 |
| WO | WO 2010/125086 A1 | 11/2010 |
| WO | WO 2012/122044 A2 | 9/2012 |
| WO | WO 2012/146655 A1 | 11/2012 |

OTHER PUBLICATIONS

Caruso et al., "Changes in Mechanical Properties and Cellularity during Long-term Culture of Collagen Fiber ACL Reconstruction Scaffolds," Wiley Interscience, vol. 74, No. 4, Jun. 15, 2005 (Published online May 6, 2005), pp. 388-897.

English translations of the Chinese Office Action and Search Report, dated Jan. 2, 2019, for Chinese Application No. 201610756407.6.

Extended European Search Report, dated Feb. 16, 2017, for European Application No. 16184119.2.

Gross et al., "Extraction of Collagen from Connective Tissue by Neutral Salt Solutions," Proceedings of the National Academy of Sciences, vol. 41, No. 1, Jan. 15, 1955, pp. 1-7 (8 pages total).

Hattori et al., "Alkali-Treated Collagen Retained the Triple Helical Conformation and the Ligand Activity for the Cell Adhesion via $\alpha^2\beta1$ Integrin," J Biochem., vol. 125, No. 4, 1999, pp. 676-684.

Karagiannis et al., "Experience from the Use of Absorbable Type I Collagen as Haemostatic Agent in Obstetric and Gynecological Operations," HIPPOKRATIA 2006, vol. 10, No. 2, 2006, pp. 182-184.

Ohan et al., "Glucose Stabilizes Collagen Steralized with Gamma Irradiation," J Biomed Mater Res A, vol. 67, No. 4, Dec. 15, 2003, pp. 1188-1195.

Retsch Inc, Centrifugal Mill Brochure, with evidence of attachment at p. 23 to show the product was used before Nov 1, 2006, https://www.pcimag.com/articles/87099-grinding-of-powder-coatings, downloaded from internet on Jun. 6, 2015, 28 pages.

Shoulders et al., "Collagen Structure and Stability," Annu. Rev. Biochem, vol. 78, 2009 (First published online Apr. 3, 2009), pp. 929-958.

Van Der Rest et al., "Collagen Family of Proteins," The FASEB Journal, vol. 5, Oct. 1991, pp. 2814-2823.

Written Opinion of the International Searching Authority and International Search Report, dated Oct. 26, 2017, for International Application No. PCT/EP2017/070428.

Russian Search Report for Russian Application No. 2019105215, dated Oct. 7, 2020.

Spotnitz et al., "Hemostats, sealants, and adhesives: components of the surgical toolbox," Transfusion, vol. 48, Jul. 2008, pp. 1502-1518.

\* cited by examiner

HEMOSTATIC FLOWABLE

FIELD OF THE INVENTION

The present invention relates to the field of hemostatic compositions, to the use of specific compounds or compositions as a hemostatic agent, to a method for preparing a hemostatic composition and to a hemostatic method.

TECHNICAL BACKGROUND

Wounds, whether external or internal, traumatic or surgical, frequently lead to bleeding. Such bleeding can be more or less significant. Bleeding is prevented and stopped via a set of physiological phenomena called "hemostasis". Hemostasis helps repair the vascular breach and, generally, ensures the maintenance of vessel and tissue integrity.

When a blood vessel is injured, a natural mechanism comprising various stages is triggered to stem the flow of blood. First, vasoconstriction, which slows the bleeding, lasts for 15 to 60 seconds and induces a complex cascade of reactions. A fibrous mesh composed of fibrin forms around the platelet plug: the final thrombus is formed and is protected from premature dissolution by factor XIII, which stabilizes fibrin. Finally, the fibrin mesh draws tighter (retraction) and the edges of the wound come together: the wound shrinks. Within the stable, cross-linked fibrin, fibroblasts can then grow and organize into a conjunctive matrix within the thrombus and finally close the wound.

No solid fibrin is present in circulating blood; if it were it would immediately obstruct vital vessels. However, fibrin's precursor, fibrinogen, is present. Under the action of thrombin, whose synthesis is activated by coagulation factors, fibrinogen is transformed into insoluble fibrin.

Lastly, several days or weeks after successful healing of the wound, the fibrin cluster is destroyed during fibrinolysis.

In spite of this biochemical phenomenon, it is often necessary, in particular in the case of wounds that are too large or in the case of diffuse bleeding, to "artificially" carry out hemostasis.

There are "mechanical" solutions to help obtain hemostasis, such as pressure, ligature and electrocoagulation, which are used as first-line treatments. However, these solutions have little or no effectiveness in a certain number of cases, such as oozing capillary hemorrhages, hemorrhages of hypervascularized organs such as the spleen or liver, hemorrhages leading to diffuse bleeding, for example bones, and/or in neurosurgery.

"Chemical" solutions, in particular implemented in certain current hemostatic products, also exist. The components of said chemical solutions are in general either of the "absorbent" or "active" type.

Absorbent hemostatic products, notably comprising polysaccharides such as regenerated oxidized cellulose or alginates, function mainly by mechanical action and simple absorption. They frequently present a problem of excessive swelling. If said swelling leads to rapid absorption of liquid, in particular blood, it can also lead to undesirable pressure when used in a "closed" environment, for example in contact with the dura mater or in urology.

In addition, certain products, notably those comprising plant polysaccharides such as cellulose or alginates, can further cause inflammatory reactions during their resorption and/or can lead to degradation products not recognized by the host. The consequence of this is that it is desirable to remove such products so that they do not remain in the body and thus do not produce these adverse effects.

Active hemostatic products, such as products containing thrombin or fibrin, are often blood-derived products. Such products involve risks of allergies and disease transmission, in particular in the case where the disease vector would not be inactivated by classically applied treatments. In addition, said downstream treatments are generally complex and/or costly. Lastly, in general they can require preparation before use, which can be a constraint, indeed a nuisance, in terms of an emergency.

Moreover, products containing both fibrin and thrombin base their mode of action on the interaction between the two blood-derived products comprising the product. The reaction can occasionally take place without interaction with the blood, in which case the products are said to float. In other words, the product is pushed away by the blood which continues to flow, possibly causing the product to become diluted or to coagulate and form a gel on top of the blood, a situation in which the flow of blood is not blocked. Hemostasis can thus not be achieved.

An hemostatic powder, its method of production and method of use, have been disclosed in the international application published under the reference WO 2012/146655 on 1 Nov. 2012, the content of which is entirely incorporated by reference in the present application.

Such hemostatic powder has a satisfactory absorption capacity, good hemostatic capacity, almost no adverse effects, good capacity to anchor on the edge of the wound and satisfactory penetration in the blood flow where it is used and/or limited swelling.

In addition to these good hemostatic properties, such hemostatic powder presents the advantage of having a very good flowability that enables it to be sprayed on the bleeding region. It can be administered in most surgical procedures, such as laparotomies, laparoscopies, coelioscopies, and robotic surgical techniques The hemostatic powder can be directly applicable on the bleeding region without specific preparation by the surgeon which is another advantage.

It might sometimes be necessary to use specific powder dispensers to ease the application of the hemostatic powder on a very specific bleeding region.

The aim of the present invention is to propose an hemostatic product that is simple to use, and especially does not need a complex preparation process, which can further be easily applied on a specific area to cover the whole bleeding region of interest.

Another aim of the present invention is to propose an hemostatic product that has a good hemostasis efficacy, and an enhanced efficacy compared to existing hemostatic products.

Still another aim of the present invention is to propose a kit for preparing an hemostatic product that can be used immediately without extensive preparation, with minimal handling of the hemostatic product, and which can be, for example, of used in several surgical procedures.

SUMMARY OF THE INVENTION

To this end, we propose a kit and a method for preparing an hemostatic flowable as defined in the appended claims.

More specifically, we propose a kit to prepare an hemostatic flowable comprising:

A hemostatic powder having a composition comprising:
  collagen of the fibrillar type comprising a content of fibrous collagen and/or fibrillar collagen of at least 70% by weight relative to the total weight of the collagen;

at least one monosaccharide; and at least one glycosaminoglycan;

A saline solution to be mixed with the hemostatic powder in order to form the hemostatic flowable.

Preferably, the collagen used for the hemostatic powder composition is not cross-linked. Using non-cross-linked collagen in the composition aims in particular at simplifying the manufacturing process.

In another preferred aspect, the saline solution is pure, consisting in a mix of distilled water and sodium chloride only, meaning that there is no additives component in the solution.

Preferable but non-limiting aspects of such a kit, taken alone or in combination, are the following:

in the composition of the hemostatic powder:
the collagen is in an amount ranging from 80% to 90% by weight relative to the total weight of the composition of the hemostatic powder;
the at least one monosaccharide is in an amount ranging from 1% to 12.5% by weight relative to the total weight of the composition of the hemostatic powder; and
the at least one glycosaminoglycan is in an amount ranging from 2% to 25% by weight relative to the total weight of the composition of the hemostatic powder.

in the composition of the hemostatic powder:
the collagen is in an amount ranging from 80% to 90% by weight relative to the total weight of the composition of the hemostatic powder;
the at least one monosaccharide is in an amount ranging from 2.5% to 7.5% by weight relative to the total weight of the composition of the hemostatic powder; and
the at least one glycosaminoglycan is in an amount ranging from 5% to 12.5% by weight relative to the total weight of the composition of the hemostatic powder.

in the composition of the hemostatic powder:
the collagen is in an amount ranging from 84% to 88% by weight relative to the total weight of the composition of the hemostatic powder;
the at least one monosaccharide is in an amount ranging from 4% to 6% by weight relative to the total weight of the composition of the hemostatic powder; and
the at least one glycosaminoglycan is in an amount ranging from 8% to 10% by weight relative to the total weight of the composition of the hemostatic powder.

in the composition of the hemostatic powder, the at least one monosaccharide is glucose and the at least one glycosaminoglycan is chondroitin sulfate.

in the composition of the hemostatic powder, the at least one glycosaminoglycan is chosen among chondroitin sulfate, dermatan sulfate, hyaluronic acid and mixtures thereof.

the composition of the hemostatic powder further comprises at least one coagulation factor in an amount lower than 0.1% by weight relative to the total weight of the composition of the hemostatic powder.

the coagulation factor is thrombin.

the saline solution comprises—or consists of—distilled water and sodium chloride, wherein the sodium chloride is in an amount ranging from 0.5% to 1.5% by weight relative to the total weight of the saline solution, most preferably in an amount of 0.9% by weight relative to the total weight of the saline solution.

the kit comprises between 1 g and 2 g of the hemostatic powder and 4 mL and 10 mL of saline solution.

the mass of the saline solution is between 2 to 10 times of the mass of the hemostatic powder, and preferably between 4 to 5 times of the mass of the hemostatic powder.

the hemostatic powder is enclosed in a dispenser having a container portion formed with bellows and a nozzle portion arranged on the container portion, wherein the nozzle portion has an opening for filing the container portion with the saline solution to be mixed with the hemostatic powder in order to form the hemostatic flowable.

the container portion has a shape designed to promote hydration of the hemostatic powder with the saline solution in order to form the hemostatic flowable.

the dispenser further comprises a cap designed to be removably coupled to the nozzle portion in order to close any opening to/from the container portion.

We also propose a method for preparing an hemostatic flowable with the above kit, comprising the steps of:

a. Providing the hemostatic powder in a container;

b. Adding a quantity of the saline solution in the container enclosing the hemostatic powder, closing and shaking said container in order to promote hydration of the hemostatic powder to form the hemostatic flowable.

Preferable but non-limiting aspects of such a method, taken alone or in combination, are the following:

the method comprises a subsequent step c) wherein the container enclosing the hemostatic flowable is left to stand during a certain rest period.

in step b), the quantity of saline solution added in the container is between 50% and 100% of the quantity of the saline solution of the kit.

in step b), the quantity of saline solution added in the container is between 5 mL and 10 mL, and is preferably of 7 mL.

in step b), the container is shaken during between 10 seconds and 30 seconds, and preferably during 20 seconds.

in step c), the rest period is at least of 30 seconds, preferably at least of 60 seconds, and even more preferably at least of 90 seconds.

in step c), the rest period is between 30 seconds and 120 seconds, preferably 90 seconds.

BRIEF DESCRIPTION OF THE DRAWINGS

Other characteristics and advantages of the invention will become clear from the following description which is only given for illustrative purposes and is in no way limitative and should be read with reference to the attached drawings on which.

DETAILED DESCRIPTION OF THE INVENTION

In the following description, absent a statement to the contrary, weight percentages are given relative to the total dry weight of the composition of the hemostatic powder.

In the context of the present invention, "total dry weight of the composition of the hemostatic powder" refers to the total weight of the composition of the hemostatic powder free of solvent, in particular water, and thus the total weight relative to the anhydrous product.

In addition, the weights of the components and the resulting percentages can correspond to the anhydrous weight of these components, in other words, to the weight of the component not including the water which it could contain. This can also be applied to the percentages obtained.

The composition of the hemostatic powder can comprise a collagen content greater than or equal to 70% by weight relative to the total weight of the composition of the hemostatic powder, in particular greater than or equal to 75% by weight, in particular greater than or equal to 77% by weight, indeed greater than or equal to 80% by weight.

In addition, the composition of the hemostatic powder can comprise a collagen content less than or equal to 99% by weight relative to the total weight of the composition of the hemostatic powder, in particular less than or equal to 96% by weight, in particular less than or equal to 93% by weight, indeed less than or equal to 90% by weight.

Thus, the composition of the hemostatic powder can comprise a collagen content ranging from 70% to 99% by weight relative to the total weight of the composition of the hemostatic powder, in particular ranging from 75% to 96% by weight, in particular ranging from 77% to 93% by weight, indeed ranging from 80% to 90% by weight. Preferably, the content of collagen is around 86% by weight of the total weight of the composition of the hemostatic powder.

Collagen is the main structure protein in mammals. Collagen consists of tropocollagen (TC) molecules that have lengths around 280-300 nm and diameters of around 1.5 nm.

The term "fibrous collagen" refers to collagen in the form of fiber, corresponding to an assembly of fibrils. Fibers generally have a diameter ranging from 1 µm to 10 µm. The term "fibrillar collagen" refers to collagen in the form of fibrils. More precisely, fibrils generally have a diameter of 10 nm to 1 µm. Thus, fibrils are formed from staggered arrays of tropocollagen molecules, and these fibrils may be arranged to form collagen fibers. Fibrous and/or fibrillar collagen is generally not soluble, whereas non-fibrillar collagen is highly soluble.

The definition of fibrous collagen and fibrillar collagen can be in particular that given by Markus Buehler in "Nature designs tough collagen: explaining the nanostructure of collagen fibrils," in PNAS, Aug. 15, 2006, vol. 103, no. 33, pp. 12285-12290.

More than 28 different collagens have been discovered and are classified in 3 main categories: collagens of the fibrillar type, collagens of the non-fibrillar type, and FACIT collagens.

Collagens of the fibrillar type are collagens that mostly comprise fibrillar and/or fibrous collagens and hardly any non-fibrillar collagens (for example collagen of type I). Similarly, collagens of the non-fibrillar type are collagens that mostly comprise non-fibrillar collagens. Some collagens of the non-fibrillar type may consist only in non-fibrillar collagens (for example collagen of type IV or V).

The industrial extraction and purification of collagen generally consists in the destructuration of the initial tissues to 1) remove every or the majority of contaminant proteins and 2) to obtain the requested structuration level depending on the final use of the product. Collagen extraction is generally performed in acid or basic conditions that allow the solubilisation of monomolecular soluble collagen which is not fibrillar. The final collagen naturally contains a mix of fibrillar/fibrous collagen and non-fibrillar collagen. The proportion between fibrillar/fibrous collagen and non-fibrillar collagen depends on the tissue chosen for the extraction and the extraction process.

The final product is different than a collagen that has been obtained by an artificial mix of only fibrillar collagen and only non-fibrillar collagen. In the article entitled "Extraction of collagen from connective tissue by neutral salt solutions" (Proceedings of the NATIONAL ACADEMY OF SCIENCES Volume 41 Number I Jan. 15, 1955 by Jérôme Gross, John H. Highberger and Francis O. Schmitt), are shown the differences between fibrillar and non-fibrillar collagens obtained after a specific extraction process which leads—as described previously—to a mix of those two collagens.

In the present hemostatic powder, the collagen is of the fibrillar type, and comprises fibrous and/or fibrillar collagen in an amount of at least 60% by weight, in particular at least 70% by weight, in particular at least 75% by weight, indeed at least 80% by weight relative to the total weight of the collagen.

More particularly, the collagen comprises at least 85%, in particular at least 90%, in particular at least 95%, indeed at least 98% by weight of fibrous and/or fibrillar collagen relative to the total weight of the collagen in the composition of the hemostatic powder.

Preferably the composition comprises a content of fibrous and/or fibrillar collagen ranging from 85% to 95% by weight relative to the total weight of the collagen in the composition, and most preferably from 85% to 90% by weight.

This means that in the preferred embodiment, the composition of the hemostatic powder thus comprises a content of non-fibrillar collagen ranging from 5% to 15% by weight relative to the total weight of the collagen in the composition, and most preferably from 10% to 15% by weight.

It is very advantageous to have a composition with such proportion of fibrous and/or fibrillar collagen relative to the non-fibrillar collagen, in particular for use as a hemostatic powder preparation. Indeed, the fibrous and/or fibrillar collagen should be present in a sufficient amount to perform the hemostasis, and the non-fibrillar collagen should also be in a sufficient amount for the cohesion of the product and not in a too large amount to avoid excess of swelling.

The collagen can be selected among type I collagens or type I and III collagens. The collagen can be extracted from various source tissues, in particular skin and/or tendons, from all species, more particularly porcine, bovine or equine species.

The collagen can mostly be made of fibrous collagen of porcine origin extracted from skin and/or tendons. In the case of collagen extracted from tendons, the extraction can be such as described in international application WO 2010/125086.

The aforesaid collagen, in particular fibrous and/or fibrillar collagen, can come from acid or basic extraction. According to a particular embodiment, said collagen comes from basic extraction. According to a particular embodiment, the collagen can be such as described in patent application FR2944706.

Preferably, the collagen comes from a basic extraction that enables maximizing the content of fibrous and/or fibrillar collagen in the extracted collagen. Further, such basic extraction can be optimized for controlling the proportion of the fibrillar/fibrous collagen and the non-fibrillar collagen within the extracted collagen. Unlike the acidic extraction, the basic extraction allows the hydrolysis of proteoglycans. This action leads to the destructuration of the tissue and the separation of the fibers without modification of their shape. In acidic conditions, the swelling of the inner collagen molecules in the fibers leads to their partial destructuration during the process with the release of greater amount of non-fibrillar soluble collagen.

The collagen can be used as it is after extraction, i.e. without further treatment, or it can be cross-linked, notably by classic modes of cross-linking such as thermal dehydration, the use of bridging agents, for example formaldehyde and/or glutaraldehyde; by oxidized polysaccharides, for example according to the method described in international application WO 2010/125086; and/or by oxidized amylopectins or glycogen. Cross-linking the collagen is however not preferred as it complexifies the manufacturing process, without necessarily increasing the hemostatic efficacy.

Preferably, the collagen used in the composition does thus not undergo any further treatment, and in particular it is not cross-linked. Using non-cross-linked collagen has notably the advantage of simplifying the manufacturing process.

The composition of the hemostatic powder comprises at least one monosaccharide, alone or in mixture with other monosaccharides. Said monosaccharides can be selected from ribose, sucrose, fructose, glucose and mixtures thereof. The monosaccharide present in the composition of the invention, alone or in mixture with monosaccharides, is in particular glucose.

The composition of the hemostatic powder can comprise a monosaccharide content ranging from 1% to 12.5% by weight relative to the total weight of the composition, in particular ranging from 1.5% to 10% by weight, in particular ranging from 2% to 8% by weight, and quite particularly ranging from 2.5% to 7.5% by weight. Most preferably, the monosaccharide content is around 5% by weight relative to the total weight of the composition.

The composition of the hemostatic powder can comprise a collagen/monosaccharide weight ratio ranging from 5 to 100, in particular from 7 to 65, more particularly from 10 to 50, and still more particularly from 11 to 40. Most preferably, the composition comprises a collagen/monosaccharide weight ratio of around 19.

The monosaccharide, notably ribose, sucrose, fructose, glucose and mixtures thereof, and in particular glucose, can notably make it possible to obtain particles comprising mainly fibrous and/or fibrillar collagen and monosaccharides with the desired characteristics, notably of size and density. Incorporation of monosaccharide in the mixture of collagen further allows reduction of the electrical charges within the composition, which enables forming a powder adapted to be placed within container such as tubes, blower, spraying or application dispensers.

Quite particularly, the presence of monosaccharide can make it easier and/or cheaper to obtain particles of a desired density and/or size, in particular in terms of improving the hemostatic properties of a powder of the composition.

Grounding collagen fibers without any additives leads to the reduction of the size of the fibers and lowers the density of the powder. Further, the final preparation contains important amount of electrical charges that prevent the manipulation of the final product. Adding monosaccharide before grinding of the collagen leads to a hardening of the preparation to mix allowing a rapid grinding (limitation of denaturation), thus enabling preparation of a powder with reduced electrical charges (suitable for placing the powder into containers, such as dispensers) and a final density suitable for applying and reconstituting the composition.

Unlike what could have been expected such adjunction of monosaccharide has no effect on the final activity of the product. In particular, it does not modify the bioactivity of the final product. The monosaccharide has no hemostatic effects.

Further, such adjunction of the monosaccharide does not make it behaving as a foaming agent as it is the case in WO 01/97873. In WO 01/97873, the heating of the diluted solution leads to the formation of gelatin. High concentration of gelatin can be made to obtain very concentrated solution, but the final product contains gelatin and not collagen. Gelatin is known to be less hemostatic than collagen as platelet aggregation needs the presence of collagen fibrils and structure of the native collagen which are absent in gelatin.

According to one embodiment, the composition comprises, preferably consists of, particles comprising, preferably consisting of, collagen and monosaccharide, notably selected from ribose, sucrose, fructose, glucose and mixtures thereof, in particular glucose.

The composition can comprise at least one coagulation factor. Said coagulation factors are well known to those persons skilled in the art. Preferably, one of the coagulation factors is thrombin. Even more preferably, the composition of the hemostatic powder comprises only thrombin as coagulation factor.

Said coagulation factor, in particular thrombin, can come from animal sources (extracted from animal tissues and fluids) or from recombinant sources (produced by cultures of genetically modified cells). The coagulation factor may for example be thrombin extracted from human tissues and fluids.

When a coagulation factor, in particular thrombin, is present, its content is preferably less than 0.1% by weight relative to the total weight of the composition of the hemostatic powder.

In the case of thrombin, international units (IU) are generally used. Thus, the composition can comprise a thrombin content ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg. Most preferably the content of thrombin—if any—is around 0.83 IU/mg of the composition.

In addition to the monosaccharide, the composition can comprise at least one other carbohydrate compound, which can be a glycosaminoglycan. Such carbohydrate compound may be part of the composition, with or without a coagulation factor such as thrombin.

Said glycosaminoglycan can be selected from chondroitin sulfates, dermatan sulfate, hyaluronic acid and mixtures thereof, in particular chondroitin sulfates.

Glycosaminoglycans can make it possible to improve the speed at which blood is absorbed by the hemostatic composition. More particularly, glycosaminoglycans can accelerate contact between the blood and the hemostatic products, in particular collagen and thrombin.

The composition can comprise a glycosaminoglycan content ranging from 2% to 25% by weight relative to the total weight of the composition, in particular ranging from 3% to 20% by weight, in particular ranging from 4% to 15% by weight, quite particularly ranging from 5% to 12.5% by weight. Most preferably the content of glycosaminoglycan—if any—is around 9% by weight of the total weight of the composition.

The composition can comprise a collagen/glycosaminoglycan weight ratio ranging from 2.5 to 50, in particular from 3.5 to 35, more particularly from 5 to 25, and still more particularly from 6.5 to 20.

According to one embodiment, the composition comprises at least one, in particular one, monosaccharide and at least one, in particular one, glycosaminoglycan, notably such as defined above, and in particular in the amounts defined above.

The carbohydrate compounds are quite particularly monosaccharides and glycosaminoglycans.

The composition can comprise a carbohydrate content ranging from 2% to 25% by weight relative to the total weight of the composition, in particular ranging from 5% to 23% by weight, in particular ranging from 7% to 21% by weight, quite particularly ranging from 10% to 18% by weight.

The composition can comprise a collagen/carbohydrate compound weight ratio ranging from 2 to 40, in particular from 2.5 to 30, more particularly from 3 to 20, and still more particularly from 3.5 to 15.

The expression "total weight of carbohydrate compounds" refers to the sum of the weight of the monosaccharides defined above and the weight of the other carbohydrate compounds mentioned above.

According to one embodiment, the composition comprises, preferably consists of:
- collagen comprising mainly a fibrous and/or fibrillar collagen content of at least 50% by weight relative to the total weight of the collagen, and
- at least one, in particular one, monosaccharide.

Quite particularly, the composition comprises, preferably consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen comprises a fibrous and/or fibrillar collagen content of at least 50% by weight relative to the total weight of the collagen, and
- at least one monosaccharide, in particular glucose, in an amount ranging from 1% to 12.5% by weight relative to the total weight of the composition, notably ranging from 1.5% to 10% by weight, in particular ranging from 2% to 8% by weight, and quite particularly ranging from 2.5% to 7.5% by weight.

According to another embodiment, the composition comprises, preferably consists of:
- collagen comprising mainly a fibrous and/or fibrillar collagen content of at least 50% by weight relative to the total weight of the collagen,
- at least one, in particular one, monosaccharide,
- at least one, in particular one, coagulation factor.

Quite particularly, the composition comprises, preferably consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen content comprises a fibrous and/or fibrillar collagen content of at least 50% by weight relative to the total weight of the collagen,
- at least one monosaccharide, in particular glucose, in an amount ranging from 1% to 12.5% by weight relative to the total weight of the composition, in particular ranging from 1.5% to 10% by weight, in particular ranging from 2% to 8% by weight, and quite particularly ranging from 2.5% to 7.5% by weight, and
- at least one, in particular one, coagulation factor, in particular thrombin, in an amount ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg.

According to another embodiment, the composition comprises, preferably consists of:
- collagen comprising mainly a fibrous and/or fibrillar collagen content of at least 50% by weight relative to the total weight of the collagen,
- at least one, in particular one, monosaccharide, and
- at least one, in particular one, glycosaminoglycan.

Quite particularly, the composition comprises, preferably consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen content comprises a fibrous and/or fibrillar collagen content of at least 50% by weight relative to the total weight of the collagen,
- at least one monosaccharide, in particular glucose, in an amount ranging from 1% to 10% by weight relative to the total weight of the composition, in particular ranging from 1% to 12.5% by weight, in particular ranging from 1.5% to 10% by weight, in particular ranging from 2% to 8% by weight, and quite particularly ranging from 2.5% to 7.5% by weight, and
- at least one glycosaminoglycan, in particular chondroitin sulfate, in an amount ranging from 2% to 25% by weight relative to the total weight of the composition, in particular ranging from 3% to 20% by weight, in particular ranging from 4% to 15% by weight, quite particularly ranging from 5% to 12.5% by weight.

According to still another embodiment, the composition comprises, preferably consists of:
- collagen comprising a fibrous and/or fibrillar collagen content of at least 50% by weight relative to the total weight of the collagen,
- at least one, in particular one, monosaccharide,
- at least one, in particular one, coagulation factor, and
- at least one, in particular one, glycosaminoglycan.

Quite particularly, the composition comprises, preferably consists of:
- collagen, notably in an amount ranging from 70% to 99% by weight, in particular ranging from 75% to 96% by weight, in particular ranging from 77% to 93% by weight, indeed ranging from 80% to 90% by weight relative to the total weight, in particular to the dry weight, of the composition, wherein said collagen comprises a fibrous and/or fibrillar collagen content of at least 50% by weight relative to the total weight of the collagen,
- at least one monosaccharide, in particular glucose, in an amount ranging from 1% to 10% by weight relative to the total weight of the composition, notably ranging from 1% to 12.5% by weight, notably ranging from 1.5% to 10% by weight, in particular ranging from 2% to 8% by weight, and quite particularly ranging from 2.5% to 7.5% by weight, at least one coagulation factor, in particular thrombin, in an amount ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg, and at least one glycosaminoglycan, in particular chondroitin sulfate, in an amount ranging from 2% to 25% by weight relative to the total weight of the composition, notably ranging from 3% to 20% by weight, in particular ranging from 4% to 15% by weight, quite particularly ranging from 5% to 12.5% by weight.

According to a quite particular embodiment, the composition comprises, preferably consists of:

collagen of the fibrillar type, mostly comprising fibrous and/or fibrillar collagen, said collagen of the fibrillar type being for example obtained by extraction in basic medium, and being in an amount of around 85% by weight relative to the total weight of the composition, glucose, in an amount of around 4.9% by weight relative to the total weight of the composition, thrombin, in an amount of 0.2 IU/mg to 2 IU/mg of the composition, and chondroitin sulfate, in an amount of around 10% by weight relative to the total weight of the composition.

According to another particular embodiment, the composition comprises, preferably consists of:

collagen of the fibrillar type, mostly comprising fibrous and/or fibrillar collagen, said collagen of the fibrillar type being for example obtained by extraction in basic medium, and being in an amount of around 85% by weight relative to the total weight of the composition, glucose, in an amount of 5% by weight relative to the total weight of the composition, and chondroitin sulfate, in an amount of 10% by weight relative to the total weight of the composition.

In the context of the present invention, the expression "an amount of around X %" refers to a variation of plus or minus 20%, in other words, an amount of around 10% means from 8% to 12%, in particular a variation of plus or minus 10%, indeed plus or minus 5%.

When the coagulation factor in form of powder, in particular thrombin, is added, such powder of the coagulation factor is preferably mixed with the powder of the homogeneous molecular mixture of collagen/monosaccharide already prepared.

When both a glycosaminoglycan (e.g. chondroitin sulfate) and a coagulation factor (e.g. thrombin) are added, they are preferably firstly mixed together, and this mix is added to the previous mixture of collagen/monosaccharide (already ground into powder).

The thrombin is not stabilized neither by carbohydrate nor collagen. The thrombin is never in contact with a solution of the monosaccharide (contrary to WO 98/57678) which prevents any denaturation of the protein and a rehydration of the powder leading to an impossibility to dry it again properly.

The composition in powder form can in particular comprise, or consist of:

particles comprising, or consisting of, collagen of the fibrillar type and at least one monosaccharide, in particular glucose, wherein in particular said particles have a size, granulometry and/or density such as defined in the present description, and optionally, particles comprising, or consisting of, at least one glycosaminoglycan, in particular chondroitin sulfates, and/or at least one coagulation factor, in particular thrombin, wherein in particular said particles have a size, granulometry and/or density such as defined in the present description.

The composition of the hemostatic powder advantageously comprises at least 50% by weight of particles whose size is between 200 μm and 400 μm.

The particles constituting the hemostatic powder advantageously have a mean granulometry ranging from 10 μm to 500 μm, in particular from 50 μm to 400 μm.

Advantageously, at least 90% by weight, in particular 100% by weight, of the particles constituting said hemostatic powder can pass through a screen whose mesh is 500 μm, in particular 400 μm.

At least 90% by weight, and in particular at least 95% by weight, of the particles constituting said hemostatic powder can be retained by a screen whose mesh is 10 μm, notably 20 μm, indeed 30 μm, indeed 50 μm.

This repartition has been chosen to allow the powder to be hydrated. With particles size too small, the powder does not form a hydrated matrix consistent with the specification and aspect required.

The hemostatic composition in powder form comprises in particular:

particles comprising collagen and a monosaccharide, and optionally, at least glycosaminoglycan and/or a coagulation factor such as thrombin.

The composition of hemostatic powder can comprise:

particles comprising collagen, a monosaccharide and optionally at least one glycosaminoglycan and/or coagulation factor, particles comprising collagen, a monosaccharide and optionally a coagulation factor and optionally glycosaminoglycan particles, particles comprising collagen and a monosaccharide and particles comprising at least one glycosaminoglycan and/or coagulation factor.

In the context of the present invention, the expression "dry powder" means that the composition comprises a limited content of solvent, in particular water. Said limited content can be less than 5% by weight, in particular less than 3% by weight, and quite particularly less than 1% by weight relative to the total weight of the composition.

Said dry form can be obtained by simple evaporation of the solvent used, by dehydration by organic solvents.

As indicated above, the described hemostatic powder is formed from non-cross-linked collagen because it is much simpler in terms of manufacturing process, and it has been proven to have a good efficacy with respect to hemostasis even though the collagen of the powder was not cross-linked.

The inventors have surprisingly discovered that, despite the fact that the collagen was not cross-linked, mixing the above described specific hemostatic powder with a saline solution enabled forming an hemostatic product with a viscosity allowing its direct application on a bleeding region to promote hemostasis.

This was indeed not expected as it was on the contrary known that the preparation of an hemostatic collagen paste from a mixture of a collagen based powder and a saline solution needed the use of cross-link collagen to work and be stable. This has been in particular disclosed in the US patent published on Jan. 2, 1990 under the reference U.S. Pat. No. 4,891,359. Cross-linking is namely known to give stability to the molecules by adding chemical bonds to the corresponding molecular structure, those additional chemical bonds being usually required for the molecules to be in an aqueous form.

Consequently, according to a preferred embodiment, the dry hemostatic powder as described above, where the collagen is not cross-linked, is thus to be hydrated with a saline solution in order to form an hemostatic flowable, which will be applied on the bleeding region.

The term "flowable" as used herein applies to compositions whose consistencies enable the composition to sustain a certain shape without any stress applied, while being deformable if a stress, such as pressure, is applied on the composition.

A flowable is not a liquid, nor a sponge, nor a powder, rather a kind of paste, gel or matrix that presents a certain viscosity. Preferably the flowable has a viscosity comprised between 20 Pa·s and 10000 Pa·s (corresponding to a range of fluidity between 0.0001 $(Pa·s)^{-1}$ and 0.05 $(Pa·s)^{-1}$).

A flowable refers to a composition that is for instance capable of passing through a syringe and/or cannula.

In the present description, we refer indifferently to a hemostatic flowable, a flowable hemostat, and a hemostatic matrix to designate the same particular composition.

The mixing of the hemostatic powder and the saline solution is thus performed to make an hemostatic flowable as defined above.

The saline solution is preferably a standard sterile saline solution used in operating room.

It is preferably composed of distilled water with an amount of sodium chloride between 0.5% and 1.5%, and preferably around 0.9%.

The saline solution is preferably pure, meaning that it consists of a mix of sodium chloride in distilled water, without the addition of any other components.

The saline solution can be stored in different forms, such as bulk in a large container, or in a specific container of a determined volume, such as pre-filled syringes.

Preferably, the saline solution is part of a kit to produce the hemostatic flowable, such a kit also comprising a specific amount of the hemostatic powder in a container.

Figure 1:
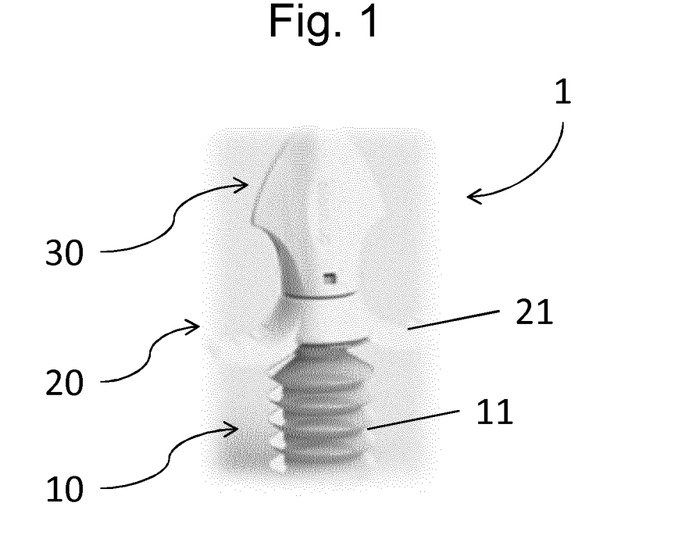
FIG. 1 is an illustration of a dispenser used to apply the hemostatic flowable presented here.
Figure 2:
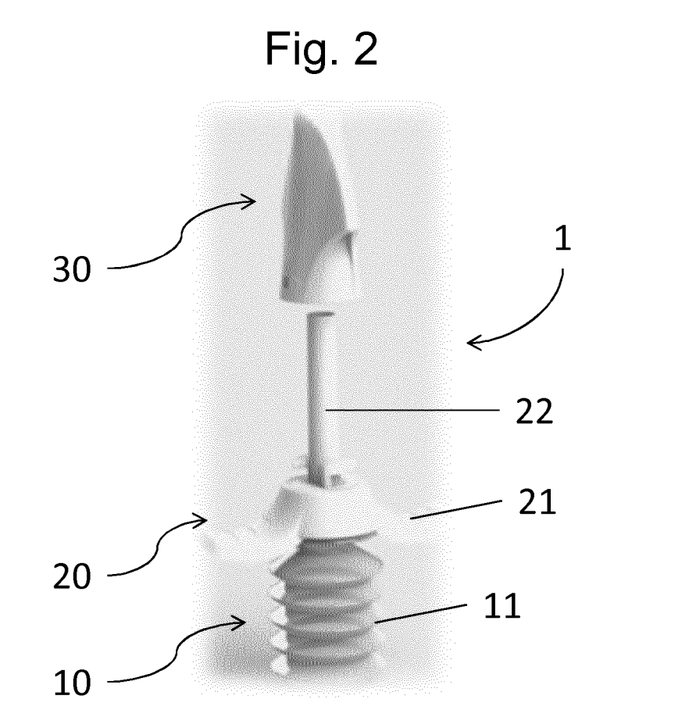
FIG. 2 is an illustration of the dispenser of FIG. 1 with the cap being open.

Preferably, the hemostatic powder of the kit is stored in a specific dispenser as illustrated in FIGS. 1 and 2.

Before the hemostatic flowable is prepared, all the active components are thus contained all together, in a powder form, within the dispenser. This is very advantageous for several aspects. It first eases the storage of the product, as one has to particularly take care of the container having the hemostatic powder, and not really of the saline solution, which is a commonly available product. This is also very advantageous in terms of manufacturing as only the hemostatic powder has to be sterilized before storage, which would for example not be the case if some components were first mixed with a saline solution (e.g. thrombin), and then mixed to an hemostatic powder.

Preferably, the dispenser 1 has a container portion 10 and a nozzle portion 20 which is adapted for application of the hemostatic flowable from the container portion 10.

Figure 5:
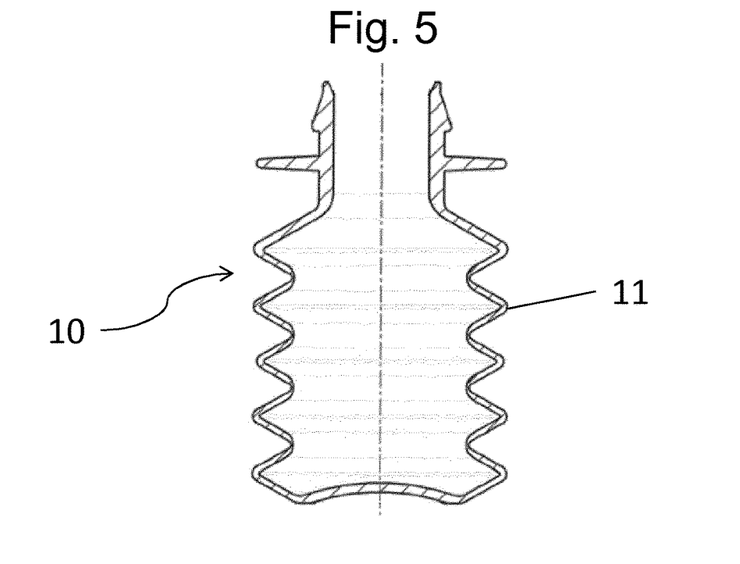
FIG. 5 is a cross-section of the container portion of the dispenser of FIG. 1.

The container portion 10, better illustrated on FIG. 5, has preferably a shape that favors the mixing of the saline solution with the hemostatic powder and enhances the hydration speed of the hemostatic powder.

In addition, the container portion 10 can have bellows 11 that enables the user to apply the hemostatic flowable by a mere manual compression of the bellows 11 in order to push the hemostatic flowable out of the dispenser 1 through the nozzle portion 20.

The nozzle portion 20 is thus designed to allow the hemostatic flowable to flow out of the dispenser upon compression of the bellows 11 of the container portion 12.

To ease the manual compression of the bellows 11 by the user, the nozzle portion 20 can comprise a finger-rest element 21 so that at least one but preferably two fingers can be positioned on the finger-rest element 21 to hold the dispenser 1 against the compression force applied on the bellows 11.

Figure 4:
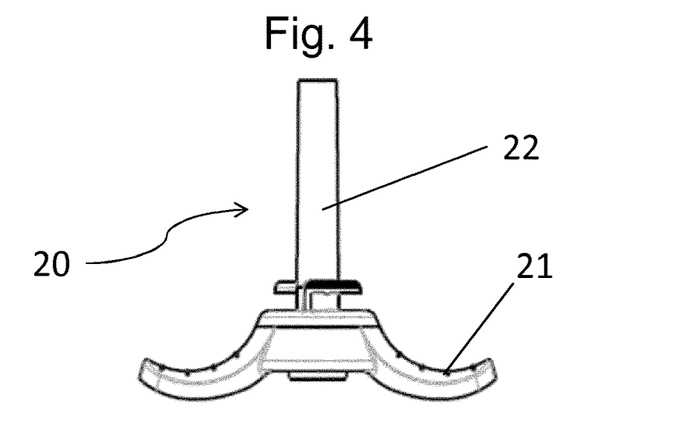
FIG. 4 is a schematic side view of the nozzle portion of the dispenser of FIG. 1.

Preferably, as illustrated on FIG. 4, the finger-rest element 21 comprises two elongated members protruding radially from the longitudinal axis of the dispenser 1, said longitudinal axis corresponding to the axis of compression of the bellows 11.

The nozzle portion 20 is also preferably designed to enable a user to fill the container portion 10 with the saline solution through the nozzle portion 20, which avoids the necessity of removing the nozzle portion 20 from the container portion 10 and prevents risks of contamination of the hemostatic powder to be hydrated.

To this end, the nozzle portion 20 may for example comprise a duct 22 through which the saline solution can be injected inside the container portion 10. Such duct 22 is also designed so that the hemostatic flowable flows easily out of the dispenser 1, through the duct 22, when the bellows 11 are compressed.

Preferably, the dispenser further comprises a cap 30 designed to be removably coupled on the nozzle portion 20.

This cap 30 preferably enables an air-tight seal of the dispenser 1, which is particularly advantageous during the storage and mixing phases.

When the dispenser 1 is not used the cap 30 is preferably closed as illustrated on FIG. 1. This can help limit the risks of contamination of the interior of the device.

Figure 3:
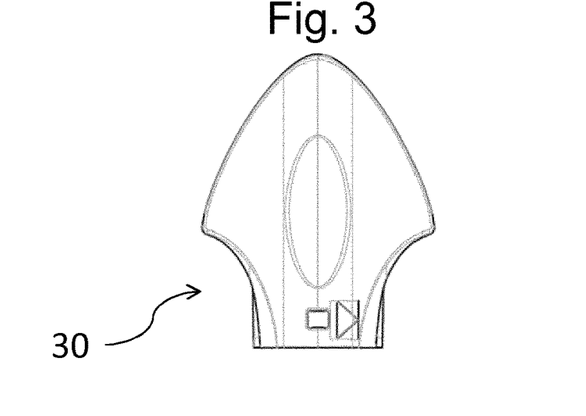
FIG. 3 is a schematic side view of the cap of the dispenser of FIG. 1.

The cap 30 used in the dispenser and illustrated on FIG. 3 is preferably a twist-off cap which eases its removal, opening and closure.

The amount of hemostatic powder for one kit is preferably between 1 g and 2 g.

The amount of saline solution for one kit is preferably between 4 mL and 10 mL, more preferably between 5 mL and 10 mL.

According to a preferred example, the kit comprises 1.65 g of hemostatic powder to be mixed with 7 mL of pure saline solution.

Preferably, in a kit, the mass of saline solution to be used for hydrating the hemostatic composition is between 2 and 10 times of the mass of the hemostatic powder, preferably between 4 and 5 times of the mass of the hemostatic powder.

When a user, e.g. a surgeon, wants to use the proposed hemostatic flowable, he can prepare it using the kit described above.

To this end, the user opens the application dispenser (also called applicator) containing the hemostatic powder by removing the corresponding cap 30.

The user has then to transfer a quantity of sterile saline solution into the dispenser 1.

Depending on the quantity of hemostatic powder in the dispenser 1, the quantity of saline solution to be used is between 5 mL and 10 mL, preferably 7 mL.

To transfer the saline solution into the container portion 10 of the dispenser 1, the user can for instance use a syringe. Such syringe is preferably provided in the kit, so that it has a volume corresponding to the exact quantity of saline solution necessary to form the hemostatic flowable by hydration of the hemostatic powder.

While transferring the saline solution into the dispenser 1, the container portion 10 is preferably rotated, for instance around its own axis, in order to ease the incorporation of the saline solution into the hemostatic powder. If the saline solution is incorporated manually by a user, the rotation of the container portion 10 can also be done by hand. The process could however be automated in required.

Tapping and/or slightly shaking the container portion 10 while transferring the saline solution could also be advantageous to promote incorporation of the saline solution into the hemostatic powder.

Once the saline solution is transferred into the dispenser 1, the opening of the nozzle portion 20 is closed, preferably by using the cap 30 of the dispenser 1, and the container is shaken to mix the hemostatic powder with the saline solution.

The shaking is preferably done for a duration of at least 15 seconds, even more preferably at least 30 seconds. A shaking time of between 10 second to 30 seconds, for example 20 seconds, is however already efficient in terms of hydration of the hemostatic powder.

The shaking is preferably performed by hand but could also be automated.

When done manually, the mixing could consist in moving the dispenser 1 up and down a certain amount of times. For instance, the dispenser 1 could be moved up and down at least between 10 to 30 times, preferably 20 times. To increase the efficiency of the mixing, the dispenser 1 could also be flipped over and then moved up and down a certain amount of times. In this second phase of manual mixing, the dispenser 1 could also be moved up and down at least between 10 to 30 times, preferably 20 times.

After the shaking, the dispenser 1 enclosing the hemostatic flowable having been formed is preferably left to stand for at least of 30 seconds, preferably at least of 60 seconds, and even more preferably at least of 90 seconds.

The standing time is likely to be between 30 seconds and 120 seconds, preferably around 90 seconds.

This rest period enables the hydration of the hemostatic powder and initial swelling to form the hydrated hemostatic flowable.

The hemostatic flowable thus formed has the advantage of being homogeneous. In particular, the hemostatic flowable has substantially an homogeneous fluidity within the dispenser. This is particularly advantageous as the application of the hemostatic flowable will thus be the same whether it is the beginning of the product from the dispenser or the remaining of the product.

Once the hemostatic flowable has been formed through hydration of the hemostatic powder with the saline solution, the hemostatic flowable is usable for a few hours, e.g. at least 8 hours, without any loss of properties or performance.

When the hemostatic flowable is ready, it can be used as follows:

Step 1: Blot excess blood from the target bleeding site with a gauze/pad or suction so that the hemostatic flowable may be applied directly to the source of bleeding. The wound surface should be as dry as possible before application.

Step 2: Apply the hemostatic flowable to the source of bleeding by squeezing the bellows. Enough product should be applied to cover the entire source of bleeding.

Step 3: Immediately use a gauze/pad, preferably wet with saline and never with blood, to hold the hemostatic material at the target bleeding site against the bleeding surface, conforming it to the lesion.

Step 4: Maintain the hemostatic material at the target bleeding site for a certain duration, for example at least two to three minutes, in order to form a hemostatic clot complex. Gently lift the gauze and inspect the area.

Step 5: If hemostasis has not been achieved, repeat steps 1-4 or use an alternate method of hemostasis treatment.

Step 6: Discard any unused product after opening.

Depending on the viscosity (resp. fluidity) of the hemostatic flowable, step 3 can be avoided, notably if the hemostatic flowable is viscous enough to hold in place without applying any gauze/pad.

For better results, it is recommended not to disrupt the clot complex by physical manipulation.

In addition, once the bleeding has ceased, any excess of the hemostatic flowable not incorporated in the hemostatic clot should be removed by gentle irrigation.

One advantage of the hemostatic flowable as proposed is that it can be used in one time, i.e. by using the whole product contained in the dispenser at once, or in many times, e.g. when there are several bleeding regions to treat at the same time or when there are several sequential bleedings during a surgery.

The hemostatic flowable as described above have the advantage of enhancing the contact surface with the wound, in particular, the contact with the bleeding area goes deeper. This is in particular of interest when the bleeding area corresponds to soft tissues and parenchymal organs.

In addition, the hemostatic flowable can be easily applied on the wound or in the bleeding area, for example directly by the surgeon manual of with a specific applicator. It enables for instance covering the whole bleeding area without leaving any region uncovered by the hemostatic flowable.

Another advantage of the proposed hemostatic flowable is that it fits the habits of the surgeons who are used to treating bleeding with a hemostatic product in the form of a paste.

This also gives the surgeon the choice to choose the form of the hemostatic product he wants to use, depending on his habits, on the specific conditions of surgery, etc. Consequently, he could use either the hemostatic powder as described in WO 2012/146655, or the hemostatic flowable as disclosed herein.

The hemostatic powder as described above can be for example prepared according to a method comprising at least the following steps:

a) formation of an aqueous suspension comprising, preferably consisting of, collagen of the fibrillar type—mainly comprising fibrous and/or fibrillar collagen—and a monosaccharide, such as glucose, b) recovery of the product in the form of precipitate, paste or gel, notably by centrifugation or decantation, c) drying of the product, for example by evaporation.

d) grinding of the product to the desired particle-size, in particular by a hammer mill, and e) optionally, adding thrombin and/or chondroitin sulfates, notably in solid form, in particular in powder form.

The formation in step a) of an aqueous suspension comprising, the fibrous/fibrillar collagen and a monosaccharide leads to a homogeneous repartition of the monosaccharide around the collagen molecules. Further, the close contact between the molecular species of collagen and the monosaccharide leads, after dehydration, to a hard cake suitable for obtaining—by grounding—a powder with the required high density. On the contrary, mixing a collagen powder and a glucose powder does not lead to an homogeneous and sprayable powder, in particular because of the density and electrical charges.

In step a) the collagen can be present at a concentration ranging from 30 g/L to 150 g/L.

The monosaccharide can be added to the suspension or to the homogeneous collagen paste in an amount such as defined in the description, and more particularly from around 2% to 5% by weight relative to the weight of the collagen.

In step a) the monosaccharide can be present at a concentration ranging from 0.3 g/L to 10 g/L.

The aqueous suspension of collagen of step a) can be acid, and in particular comprise an acid such as hydrochloric acid. Said acid can be present at a concentration ranging from 0.01 M to 0.5 M, and in particular from 0.02 M to 0.1 M, indeed around 0.05 M. Said suspension can be in the form of homogeneous paste.

Step b) can comprise the pouring of the suspension into a mold.

Step c) is performed so as to obtain a cake as thick as possible (superior the final particle-size wanted), with a very high density and as less air bubbles as possible (less than 5%) inside the cake.

Step d) can be followed by a step of screening of the powder, notably in order to obtain the desired particle size.

According to a preferred embodiment, step a) consists in forming a mixture comprising 95% by weight of collagen of the fibrillar type and 5% by weight of glucose. After having dried (step b)) and ground (step c)) this mixture, chondroitin sulfate is added in a content of 10% by weight of the total weight of the mixture, such that the final composition comprises:
- collagen: 86.36% by weight relative to the total weight of the composition;
- glucose: 4.54% by weight relative to the total weight of the composition;
- chondroitin sulfate: 9.09% by weight relative to the total weight of the composition;

When thrombin is also added, it represents a final content lower than 0.01% by weight relative to the total weight of the composition. In the above mixture, thrombin may be in an amount of 0.083 IU/mg of the composition.

For all the aforesaid powder products, it is quite obviously possible to apply a more or less thorough grinding to obtain a powder of variable particle-size according to the type of grinding and the duration thereof.

The hemostatic flowable made from the hemostatic powder mixed with a specific amount of saline solution can be used as a hemostatic agent.

This hemostatic flowable can also be used as a pharmaceutical composition, in particular a hemostatic drug.

As described above, we also propose a hemostatic method comprising the depositing of the hemostatic flowable such as defined above on a hemorrhaging part of an animal's body, including humans. In particular, the hemostatic flowable can be used in surgical procedures, in particular laparotomies, laparoscopies, coelioscopies and robotic procedures.

The hemostatic flowable described above could also be used as a cicatrizing agent for internal and external wounds. The expression "cicatrizing agent" refers to a product that makes it possible to obtain a clinically satisfactory cicatrization of the tissues with which it is in contact.

EXAMPLES

Example 1: Protocol for Measuring Hemostatic Capacity In Vitro

Citrated (around 0.1 M) human blood is maintained at 37° C. in a water bath throughout the measurement. The product to be tested (10 mg) is deposited in a 5 mL polypropylene tube with a snap-on cap, and then citrated fresh blood (2 mL) is added. $CaCl_2$ is then added so that the final $CaCl_2$ concentration in the blood is 15 mM, and then the test tube is closed. The contents are then around mixed by vigorous inversions (10 times) and then the test tube is plunged into the water bath; the test tube is returned to the vertical position every 10 seconds. The time required to form a clot is noted and corresponds to hemostatic capacity.

Example 2: Protocol for Measuring Particle Size

A known quantity of product, notably of powder, is sifted through 50 μm, 100 μm, 200 μm, 300 μm and 400 μm screens for 2 minutes (per screen). The fractions from each screen are weighed. The proportion of each particle size range is determined.

Example 3: Protocol for Measuring the Swelling of the Composition

A 15 mL flask is weighed ($m_0$ in mg) and then X mg of powder of the dry composition is added ($m_{0+X}$ in mg). A 0.15 M aqueous NaCl solution (2 mL) is added and the composition is left to swell for 20 minutes; the flask is then centrifuged at 1,000 rpm.

Excess NaCl is removed with a Pasteur pipette and droplets are eliminated by turning over the flask on filter paper; the flask is then weighed with the wet powder ($m_1$ in mg).

The swelling ratio is calculated as follows: $((m_1-m_0)/(m_{0+X}-m_0))$.

Example 4: Preparation of Collagen of the Fibrillar Type by Basic Extraction

Pieces of pig dermis (30 kg), defatted with acetone, are left to swell for 3 hours in 100 kg of 0.05 M NaOH solution. The dermises are finely cut up by a cutting mill and the paste obtained is diluted with 50 liters of 0.05 M NaOH. The mixture is then sieved under pressure through a 1 mm screen. The paste obtained is then brought to pH 6-7.5 with HCl and the precipitate obtained is collected by centrifugation or filtration through a 1 mm screen.

The retentate is dehydrated with acetone according to methods known to those persons skilled in the art. This dehydrated retentate thus consists in collagen of the fibrillar type, with a large content of fibrillar/fibrous collagen relative to the non-fibrillar collagen. Generally, such extracted collagen comprises from 85% to 95% by weight of fibrillar/fibrous collagen relative to the total weight of the collagen, and from 5% to 15% by weight of non-fibrillar collagen relative to the total weight of the collagen.

Example 5: Preparation of a Hemostatic Powder #1

30 g of collagen of the fibrillar type as prepared in Example 4 is added to 1 L of a 0.02 M aqueous HCl solution and the mixture is then stirred for 5 hours. Next, to the homogeneous paste obtained, powdered fructose is added in an amount of 2% (0.6 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 μm.

Dermatan sulfate is then added to the powder in an amount of 2% by weight relative to the dry matter of the powder (0.612 g).

The mixture is then homogenized using a ball mill, lyophilized thrombin is added to the mixture in an amount of 15 IU/mg of powder, and finally the mixture is homogenized using a ball mill.

Example 6: Preparation of a Hemostatic Powder #2

7.5 kg of collagen of the fibrillar type as prepared in Example 4 is added to 50 L of a 0.05 M aqueous HCl solution and the mixture is then stirred for 16 hours. Next, to the homogeneous paste obtained, powdered fructose is added in an amount of 5% (375 g) by weight relative to the weight of the collagen.

The mixture is homogenized for 3 hours and then distributed onto plates and dehydrated. After drying, the dry product is ground by fraction at a rate of 5 g/min using a hammer mill at 12,000 rpm under controlled heating. The product is then screened by mechanical sifting to eliminate particles whose size is larger than 400 µm and those smaller than 50 µm.

Granulometry is measured in order to verify that the distribution is such that 60% of the sample by weight has a granulometry greater than 200 µm.

Purified chondroitin sulfates are then added to the powder in an amount of 20% by weight relative to the dry matter of the powder (1.575 kg). The mixture is homogenized using a ball mill.

Finally, lyophilized thrombin is added to the mixture in an amount of 10 IU/mg of powder. As before, the mixture is homogenized using a ball mill.

Example 7: Preparation of a Hemostatic Powder #3

1000 g of collagen of the fibrillar type as prepared in Example 4 is added to 60 mL of a 0.02 M aqueous HCl solution and the mixture is then stirred for 5 hours. Next, to the homogeneous paste obtained, powdered glucose is added in an amount of 5% (50 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm and smaller than 50 µm.

Chondroitin sulfate is then added to the powder in an amount of 10% by weight relative to the dry matter of the powder (105 g). The mixture is then homogenized using a ball mill.

Such powder composition has a tapped density of around 0.408 g/mL.

Example 8: Preparation of a Hemostatic Powder #4

500 g of collagen of the fibrillar type as prepared in Example 4 is added to 30 mL of a 0.02 M aqueous HCl solution and the mixture is then stirred for 5 hours. Next, to the homogeneous paste obtained, powdered glucose is added in an amount of 5% (25 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm and smaller than 50 µm.

Chondroitin sulfate mixed with a thrombin powder is then added to the powder in an amount of 10% by weight relative to the dry matter of the powder (52.5 g). The thrombin is added to the mixture in a final amount of 0.85 U/mg. The mixture is then homogenized using a ball mill.

Such powder composition has a tapped density of around 0.425 g/mL.

Example 9: Preparation of a Hemostatic Powder #5

750 g of collagen of the fibrillar type as prepared in Example 4 is mixed with 6675 mL of highly purified water. The mixture is stirred at a first stirring rate of 20 rpm during 10 minutes, and then at a second stirring rate of 40 rpm during 15 minutes.

The above mixture is then stirred again at the first stirring rate of 20 rpm while a solution of glucose (37.5 g of glucose with 300 mL of water) is incorporated. The quantity of glucose added corresponds to 5% by weight relative to the weight of the collagen being used in the mixture. This new mixture is stirred at the second stirring rate of 40 rpm during 10 minutes. This preparation is then stored during 16 hours.

A quantity of 87.5 mL of a 1 M aqueous HCl solution is then added to the preparation while being stirred at a stirring rate of 30 rpm. This new mixture is then stirred at a first stirring rate of 35 rpm during 1 minute, then at a second stirring rate of 40 rpm during 1 minute, followed then by several stirring sessions of 5 minutes at the same stirring rate of 40 rpm, a quick pause in the stirring being made between two sessions.

The thick paste obtained in the preceding phase is then separated in several pieces having similar shape and mass. Those pieces of the paste are then placed for 24 hours in a hermetically sealed enclosure having an atmosphere saturated with ammonia. After this neutralization step, the pieces of paste are dried at 20° C. during 96 hours, and the dry products are then ground at a rate of 1 kg/h using a cryogenic mill of Forplex at 8,500 rpm. The powder product is then screened by mechanical sifting to eliminate particles whose size is larger than 200 µm and smaller than 50 µm, resulting in a collagen-glucose powder.

A powder of chondroitin sulfate (CS) which is made of particles having a size between 50 µm and 200 µm is then added to the collagen-glucose powder in an amount of 10% by weight relative to the dry matter of the collagen-glucose powder. For instance, 30 g of the powder of chondroitin sulfate is mixed with 300 g of the collagen-glucose powder. For this hemostatic powder #5, freeze-dried thrombin is also added, in a quantity of 1000 UI/g. The mixture is then homogenized using a V blender. The final hemostatic powder has a tapped density of around 0.4 g/mL.

Example 10: Collagen Characterization→Presence of Soluble Collagen in the Collagen, Determination of the Ratio Between Fibrillar/Fibrous Collagen and Non-Fibrillar Collagen The goal of the experimentation is to determine the proportion of fibrillar/fibrous collagen and non-fibrillar collagen in a collagen (extracted collagen or collagen ground into powder). Such proportion can be determined by studying the proportion of insoluble (corresponding to the fibrillar/fibrous collagen) and soluble collagen (corresponding to the non-fibrillar collagen) in the collagen.

The experimentation consists in solubilizing about 2.5 g of the collagen under test in 166 mL of water at pH 13 during 16 hours. The solution is then centrifuged (10 000 rpm during 10 minutes). The supernatant (corresponding to the non-fibrillar collagen) and the residue (corresponding to the fibrous/fibrillar collagen) are then split. The residue is directly dried with successive acetone baths and under a controlled air flow. The pH of the supernatant is adjusted at pH 3 with acetic acid and chlorhydric acid at 6M. The solid collagen from the supernatant is obtained by adding NaCl 0.6M, and by performing a centrifugation. It is then dried with successive acetone baths and under a controlled airflow.

The collagen weights from the residue (Mresidue) and from the supernatant (Msupernatant) are calculated, and the formula Mresidue/(Mresidues+Msupernatant)×100 gives the percentage of fibrous collagen on total amount of collagen.

In the invention, the ratio Mresidue/(MResidues+Msupernatant) must be superior to 80% both for the collagen used to prepare the powder and for the final collagen powder. Preferentially the ratio is superior to 85%.

For example, the above experimentation made of three batches of collagen prepared as in example 4 gives very similar ratios of 92.67%, 94.60% and 91.51% respectively. After having ground the collagen of these three batches, the ratio remains very similar as it is of 91.63%, 88.02%, and 88.69% respectively.

Another way to show the presence of both fibrous/fibrillar collagen and soluble collagen is to perform a SDS page electrophoresis.

Figure 6:
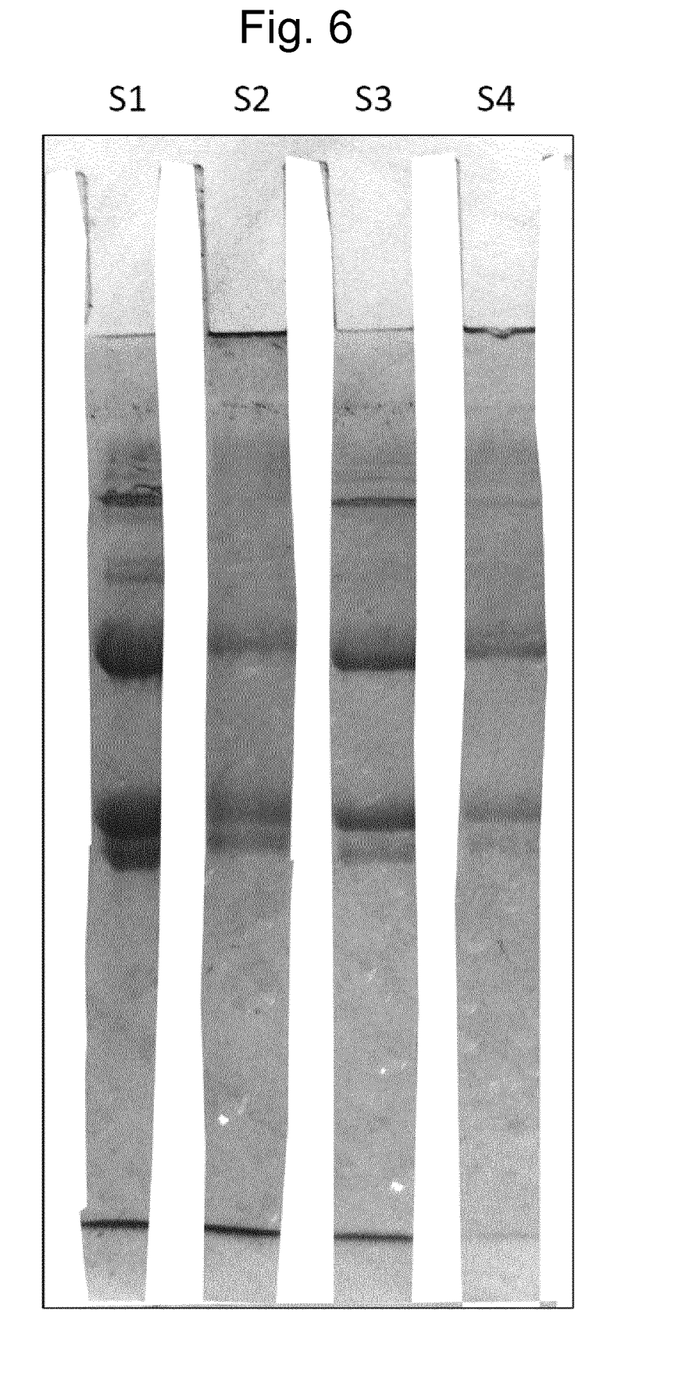
FIG. 6 is an example of a result of an electrophoresis as described in example 10.

FIG. 6 illustrates such electrophoresis, with sample S1 corresponding to the supernatant of a first batch (made from collagen extracted as in example 4), sample S2 corresponding to the residue of this first batch, and sample S3 corresponding to the supernatant of a second batch (also made from collagen extracted as in example 4), sample S4 corresponding to the residue of this second batch.

The results show that for the collagen from the residue, a larger amount of fiber cannot migrate through the acrylamide gel and are stained at the stop of the gel. The preparation of the sample does not allow the split of each chain from the collagen. Therefore, alpha chains are present in a very low amount. The collagen from the supernatant is able to entirely migrate in the gel, there are no fiber blocked at the top, chains from the collagen are properly split during the electrophoresis process.

BIBLIOGRAPHIC DATA

WO 2012/146655
"Nature designs tough collagen: explaining the nanostructure of collagen fibrils," by Markus Buehler (PNAS, Aug. 15, 2006, vol. 103, no. 33, pp. 12285-12290)
"Extraction of collagen from connective tissue by neutral salt solutions" by Jérôme Gross, John H. Highberger and Francis O. Schmitt (Proceedings of the NATIONAL ACADEMY OF SCIENCES Volume 41 Number I Jan. 15, 1955)
WO 2010/125086
FR2944706
WO 01/97873
U.S. Pat. No. 4,891,359

The invention claimed is:

1. A kit to prepare an hemostatic flowable comprising:
   a hemostatic powder having a composition comprising:
      non-cross-linked collagen of the fibrillar type comprising a content of fibrous collagen and/or fibrillar collagen of at least 70% by weight relative to the total weight of the collagen;
      at least one monosaccharide; and
      at least one glycosaminoglycan;
   a component which makes the hemostatic flowable, wherein said component consists of a saline solution to be mixed with the hemostatic powder.

2. The kit of claim 1, wherein in the composition of the hemostatic powder:
   the collagen is in an amount ranging from 80% to 90% by weight relative to the total weight of the composition of the hemostatic powder;
   the at least one monosaccharide is in an amount ranging from 1% to 12.5% by weight relative to the total weight of the composition of the hemostatic powder; and
   the at least one glycosaminoglycan is in an amount ranging from 2% to 25% by weight relative to the total weight of the composition of the hemostatic powder.

3. The kit of claim 1, wherein in the composition of the hemostatic powder:
   the collagen is in an amount ranging from 80% to 90% by weight relative to the total weight of the composition of the hemostatic powder;
   the at least one monosaccharide is in an amount ranging from 2.5% to 7.5% by weight relative to the total weight of the composition of the hemostatic powder; and
   the at least one glycosaminoglycan is in an amount ranging from 5% to 12.5% by weight relative to the total weight of the composition of the hemostatic powder.

4. The kit of claim 1, wherein in the composition of the hemostatic powder:
   the collagen is in an amount ranging from 84% to 88% by weight relative to the total weight of the composition of the hemostatic powder;
   the at least one monosaccharide is in an amount ranging from 4% to 6% by weight relative to the total weight of the composition of the hemostatic powder; and
   the at least one glycosaminoglycan is in an amount ranging from 8% to 10% by weight relative to the total weight of the composition of the hemostatic powder.

5. The kit of claim 1, wherein in the composition of the hemostatic powder, the at least one monosaccharide is glucose and the at least one glycosaminoglycan is chondroitin sulfate.

6. The kit of claim 1, wherein in the composition of the hemostatic powder, the at least one glycosaminoglycan is chosen among chondroitin sulfate, dermatan sulfate, hyaluronic acid and mixtures thereof.

7. The kit of claim 1, wherein the composition of the hemostatic powder further comprises at least one coagulation factor in an amount lower than 0.1% by weight relative to the total weight of the composition of the hemostatic powder.

8. The kit of claim 7, wherein the coagulation factor is thrombin.

9. The kit of claim 1, wherein the saline solution comprises distilled water and sodium chloride, wherein the sodium chloride is in an amount ranging from 0.5% to 1.5% by weight relative to the total weight of the saline solution, most preferably in an amount of 0.9% by weight relative to the total weight of the saline solution.

10. The kit of claim 1, comprising between 1 g and 2 g of the hemostatic powder and 4 mL and 10 mL of saline solution.

11. The kit of claim 1, wherein the mass of the saline solution is between 2 to 10 times of the mass of the hemostatic powder, and preferably between 4 to 5 times of the mass of the hemostatic powder.

12. The kit of claim 1, wherein the hemostatic powder is enclosed in a dispenser having a container portion formed with bellows and a nozzle portion arranged on the container portion, wherein the nozzle portion has an opening for filing the container portion with the saline solution to be mixed with the hemostatic powder in order to form the hemostatic flowable.

13. The kit of claim 12, wherein the container portion has a shape designed to promote hydration of the hemostatic powder with the saline solution in order to form the hemostatic flowable.

14. The kit of claim 12, wherein the dispenser further comprises a cap designed to be removably coupled to the nozzle portion in order to close any opening to/from the container portion.

15. A method for preparing an hemostatic flowable using the kit of claim 1, comprising the steps of:
  a. providing the hemostatic powder of the kit in a container;
  b. adding a quantity of the saline solution to the container and closing and shaking said container to promote hydration of the hemostatic powder to form the hemostatic flowable.

16. The method of claim 15, further comprising a subsequent step c) wherein the container enclosing the hemostatic flowable is left to stand during a certain rest period.

17. The method of claim 15, wherein in step b), the quantity of saline solution added in the container is between 50% and 100% of the quantity of the saline solution provided in the kit for forming an hemostatic flowable.

18. The method of claim 15, wherein in step b), the quantity of saline solution added in the container is between 5 mL and 10 mL.

19. The method of claim 15, wherein in step b), the quantity of saline solution added in the container is of 7 mL.

20. The method of claim 15, wherein in step b), the container is shaken during between 10 seconds and 30 seconds.

21. The method of claim 15, wherein in step b), the container is shaken during 20 seconds.

22. The method of claim 16, wherein in step c), the rest period is at least of 30 seconds, preferably at least of 60 seconds, and even more preferably at least of 90 seconds.

23. The method of claim 16, wherein in step c), the rest period is at least of 60 seconds.

24. The method of claim 16, wherein in step c), the rest period is at least of 90 seconds.

25. The method of claim 16, wherein in step c), the rest period is between 30 seconds and 120 seconds.

26. The method of claim 15, wherein
  in step a), a quantity of 1.65 mg of hemostatic powder is provided in the container;
  in step b), the quantity of saline solution added in the container is of 7 mL and the container is shaken during 20 seconds.

27. The kit of claim 2, wherein in the composition of the hemostatic powder, the at least one monosaccharide is glucose and the at least one glycosaminoglycan is chondroitin sulfate.

28. The kit of claim 2, wherein the composition of the hemostatic powder further comprises at least one coagulation factor in an amount lower than 0.1% by weight relative to the total weight of the composition of the hemostatic powder.

29. A kit to prepare an hemostatic flowable comprising:
  a hemostatic powder having a composition comprising:
    collagen of the fibrillar type comprising a content of fibrous collagen and/or fibrillar collagen of at least 70% by weight relative to the total weight of the collagen;
    at least one monosaccharide; and
    at least one glycosaminoglycan;
  a component which makes the hemostatic flowable, wherein said component consists of a saline solution to be mixed with the hemostatic powder,
wherein the hemostatic flowable has a viscosity of 20 Pa·s to 10000 Pa·s when the hemostatic powder is mixed with the saline solution.

30. A kit to prepare an hemostatic flowable comprising:
  a hemostatic powder having a composition comprising:
    non-cross-linked collagen of the fibrillar type comprising a content of fibrous collagen and/or fibrillar collagen of at least 70% by weight relative to the total weight of the collagen;
    at least one monosaccharide; and
    at least one glycosaminoglycan;
  a component which makes the hemostatic flowable, wherein said component consists of a saline solution to be mixed with the hemostatic powder,
wherein the hemostatic flowable has a viscosity of 20 Pa·s to 10000 Pa·s when the hemostatic powder is mixed with the saline solution.

* * * * *